US00PP07909P

United States Patent [19]

Roberson

[11] Patent Number: Plant 7,909

[45] Date of Patent: Jul. 14, 1992

[54] DAYLILY NAMED BLACK EYED STELLA

[76] Inventor: Robert J. Roberson, 31706 E. Pink Hill Rd., Grain Valley, Mo. 64029

[21] Appl. No.: 538,258

[22] Filed: Jun. 14, 1990

[51] Int. Cl.[5] ..... A01H 5/00

[52] U.S. Cl. ..... Plt./87.4

[58] Field of Search ..... Plt./68, 87.4

*Primary Examiner*—Howard J. Looker

[57] ABSTRACT

A new daylily cultivar having a profuse production of relatively small flowers having a generally buff yellow color and distinguished by an annular dark red band at its mid-portion surrounding a golden throat having a lime green heart; this plant being particularly characterized by a habit of blooming continuously through upwards of 100 days per year from March until frost in USDA climate zone 10 and mid-May through Fall in climate zone 6.

1 Drawing Sheet

BACKGROUND OF THE NEW PLANT

My new daylily cultivar originated as a seedling of a hybrid produced by me at my ranch at Tomball, Tex., by crossing the cultivar Stella De Oro with pollen from the cultivar Little Celina in 1983 and this seedling has been reproduced by me at my Tomball ranch by means of offsets and selections of naturally occuring divisions through several generations whereby it was determined that the novel characteristics of the original seedling would hold true from generation to generation and appeared to be firmly fixed.

Present propagation of this new plant is being done by divisions and offsets at Grain Valley, Mo., and by tissue culture at Magnolia, Tex.

DESCRIPTION OF THE DRAWING

My new Daylily cultivar is illustrated by the accompanying full color photograhic drawings of which, the right hand view shows face views of several mature blooms of the new plant; and the left hand view shows a potted assembly, or clump, of several scapes in full bloom. The color reproduction in these two views is as close to that herein specified as is reasonably possible to obtain by professional photographic procedures.

DESCRIPTION OF THE NEW PLANT

The following is a detailed description of my hybrid daylily cultivar based upon observation of plants grown at Grain Valley, Mo., in the current season, the color designations of the flower being according to the Pantone Matching System (PMS).

THE PLANT

Origin: Seedling.

Parentage:

*Seed parent.*—Daylily cultivar Stella De Oro (unpatented).

*Pollen parent.*—Little Celina (unpatented).

Classification:

*Botanic.*—Hemerocallis hybrid.

*Commercial.*—Daylily cultivar 'Black Eyed Stella'.

Form: Single stem, erect and stately scape from a fan shaped plant made up of narrow arching grass-like long keeled glabrous leaves 2-ranked at the base of the scape.

Foliage:

*Quantity.*—Abundant, a mature plant having about 12 leaves.

Leaf size: About 1¼ inches wide and about 11½ inches long.

Leaf shape: Linear and long keeled with entire margins.

Texture: Glabrous.

Color: Dark Green (PMS 371/378).

Scape:

*Color.*—Dark Green (PMS 378).

*Height.*—About 14 inches.

THE BUD

Form: Modified oblanceolate.

Size (Day before opening):

*Length.*—About 3.6 cm.

*Width.*—About 1.3 cm.

Opening rate: About 6 hours.

Color:

*When sepals first divide.*—Green (PMS 383).

Penduncle:

*Character.*—Rigid and sturdy.

*Color.*—Dark Green (PMS 378).

THE FLOWER

Blooming habit: The flowers bloom recurrently and the scape is continuously in bloom for a period upwards of 100 days.

Flower size: Small.

*Diameter.*—About 3⅛ inches.

*Depth.*—About 2 inches.

Borne: Singly on the branchlets of a sturdy, erect rachis which is ramulous; each scape has at least four or five peduncles each of which divides into twelve or fifteen pedicels.

Number of blooms per scape: One to four each day.

Petalage: The flower consists of six perianth segments consisting of three sepals (the outer segments) and three petals (the inner segments) all in an imbricated arrangement.

THE SEPALS

Shape: Oblanceolate with slightly undulated entire margins and an acuminate apex.

Size: About 1⅜ inches long and ⅝ inch wide.

Texture: Ribbed.

THE PETALS

Shape: Broadly obovate with entire undulated margins and a broadly cuspidate apex.

Texture: Slightly puckered and ribbed.
Size: About 1⅝ inch by 1⅛ inch.
Color: Buff Yellow (PMS 134) with a Dark Red (PMS 187) mid-portion and a Gold throat (PMS 136).
Effect of weather: This plant is not in any way affected by sunlight but is slightly darker in wet weather.
Fragrance: Slight.
Disease resistance: This plant is resistant to root rot as observed at Tomball, Tex.
Lasting quality: About 24 hours.

THE REPRODUCTIVE ORGANS

Stamens:
*Number.*—Six.
*Arrangement.*—Inserted individually at the summit of the perianth tube.
*Anthers.*—Arrangement: Introrse. Size: 4 mm. Color: Brown (PMS 161).
*Filaments.*—Slender and 3 cm. in length. Color: Gold (PMS 136).
*Pollen.*—Color: Golden (PMS 143).
Pistils:
*Number.*—One.
*Style.*—Length: 6 cm. Color: Gold (PMS 136).
*Stigma.*—Color: White.
Character of ovaries: Three celled.
*Shape.*—Oblong, becoming a loculieidally 3-valved capsule.

THE FRUIT (Seed Pod)

Shape: The seed pod is an ovoid capsule.
Color: Ranges from Pale Green (PMS 384) to Brown (PMS 465) at maturity.
Fertility: The seeds are fertile.

My new variety of Daylily most nearly resembles the well-known cultivar Stella De Oro, but is distinguished in particular by being a larger bloom having a very unique annular color band at its mid-portion which surrounds the throat of the bloom. Further, the new variety has a 10% larger root and plant size than does the cultivar Stella De Oro and is more resistant to root rot, in USDA zones 9 and 10 than Stella De Oro; and the extremely long period of continuous blooming has been verified by the controlled propagation of more than 5,000 cultivars of Daylilies grown for testing and verification of the fixed homogeneity of the new plant.

By direct comparison, the tested cultivars show the following distinctive characteristics:

1. My new plant (fan) increases at least 5 times per year whereas the average plant increases only about 2 times per year.

2. The average blooming period for my new plant is at least 106 days whereas the average plant has a blooming period of about 21 days.

3. My new plant produces about 2.5 blooms per day whereas the ordinary plant averages less than one per day.

4. The average time of excellent quality foliage for my new cultivar is about 18 weeks whereas the average time of excellent quality foliage for the ordinary plant is only 10 weeks.

I claim:

1. A new and distinctive Daylily cultivar, substantially as herein shown and described, particularly distinguished by a bloom of medium size having a dark red annular ring at its mid-portion surrounding a golden colored throat; and a continuous blooming period upwardly of 100 days for a plant having an average height of about 14 inches.

* * * * *

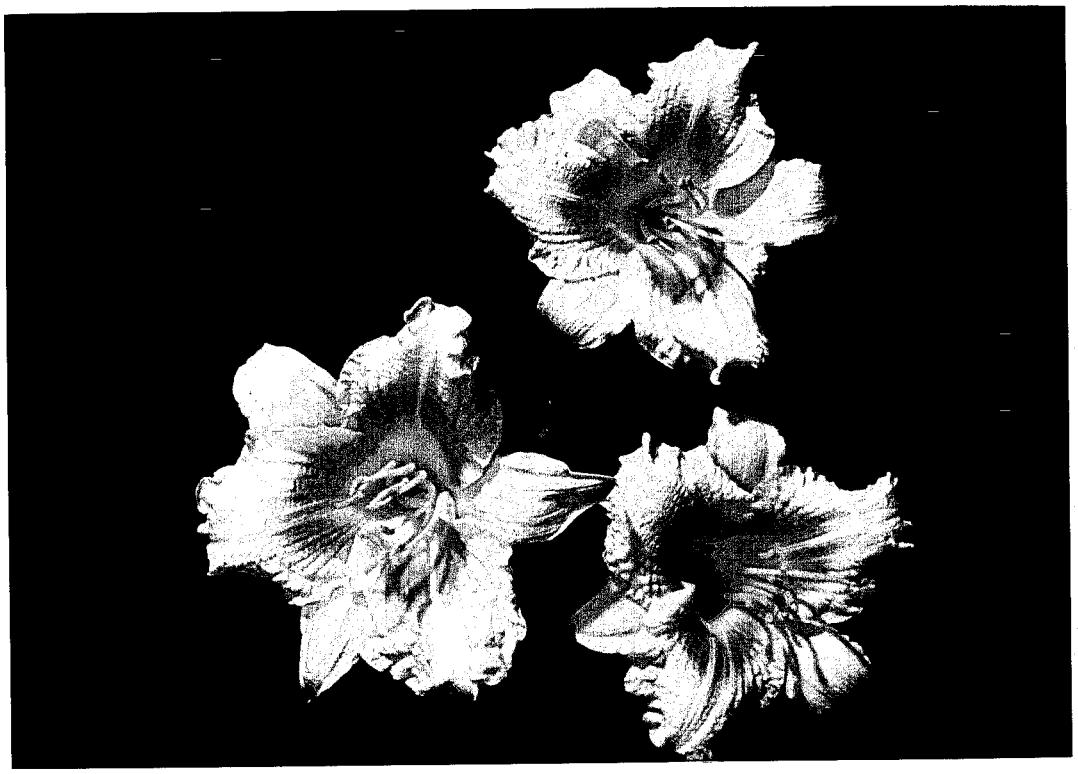
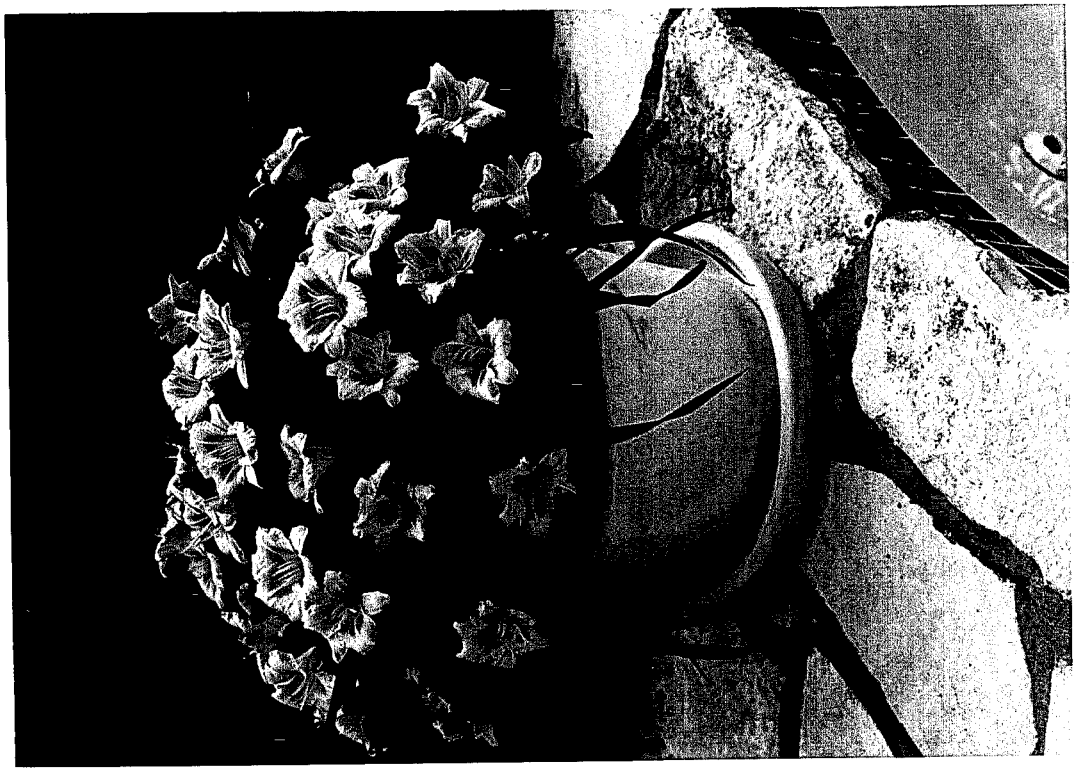

UNITED STATES PATENT AND TRADEMARK OFFICE

CERTIFICATE OF CORRECTION

PATENT NO. : Plant 7,909

DATED : 7/14/92

INVENTOR(S) : Robert J. Roberson

It is certified that error appears in the above-identified patent and that said Letters Patent is hereby corrected as shown below:

Title page: col.1, lines 6 and 7, delete "seedling of a hybrid" and insert --hybrid seedling--.

Signed and Sealed this

Seventeenth Day of August, 1993

Bruce Lehman

*Attest:*

BRUCE LEHMAN

*Attesting Officer*

*Commissioner of Patents and Trademarks*